United States Patent
Zehner et al.

(10) Patent No.: US 7,351,384 B2
(45) Date of Patent: Apr. 1, 2008

(54) HYDROFORMYLATION

(75) Inventors: Peter Zehner, Ludwigshafen (DE); Michael Nilles, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/218,532

(22) Filed: Sep. 6, 2005

(65) Prior Publication Data

US 2006/0004231 A1 Jan. 5, 2006

Related U.S. Application Data

(62) Division of application No. 10/073,248, filed on Feb. 13, 2002, now Pat. No. 7,015,361.

(30) Foreign Application Priority Data

Feb. 13, 2001 (DE) ................. 101 06 482

(51) Int. Cl.
*B01J 10/00* (2006.01)
*B01J 19/00* (2006.01)
(52) U.S. Cl. ............... 422/189; 422/193; 422/234; 422/236
(58) Field of Classification Search .............. None
See application file for complete search history.

(56) References Cited

U.S. PATENT DOCUMENTS 3,988,117 A * 10/1976 Schnur et al. ............. 422/201
6,838,061 B1 1/2005 Berg et al.

FOREIGN PATENT DOCUMENTS

| EP | 132224 A1 * | 1/1985 |
|---|---|---|
| GB | 2111852 A * | 7/1983 |
| WO | WO 97/20793 | 6/1997 |

OTHER PUBLICATIONS

Falbe, "New Synthesis with Carbon Monoxide" (1980), pp. 162-174.

* cited by examiner

*Primary Examiner*—Glenn Caldarola
*Assistant Examiner*—Jennifer A. Leung
(74) *Attorney, Agent, or Firm*—Novak Druce + Quigg LLP

(57) ABSTRACT

Olefins having at least 6 carbon atoms are hydroformylated in the presence of a homogenous catalyst in a continuous process in which a) a vertical tall cylindrical reactor (1) whose interior space is divided by means of internals (2). into at least two reaction chambers which extend essentially in the longitudinal direction of the reactor is used, b) at least one olefin is introduced into the reactor together with synthesis gas at the lower end of the first reaction chamber, c) a partially reacted reaction mixture is conveyed from the upper end of a reaction chamber to the lower end of a next reaction chamber; and d) the hydroformylated olefin is taken off at the upper end of the last reaction chamber. The process allows a high conversion at a given reactor volume.

5 Claims, 4 Drawing Sheets

HYDROFORMYLATION

Figure 1:
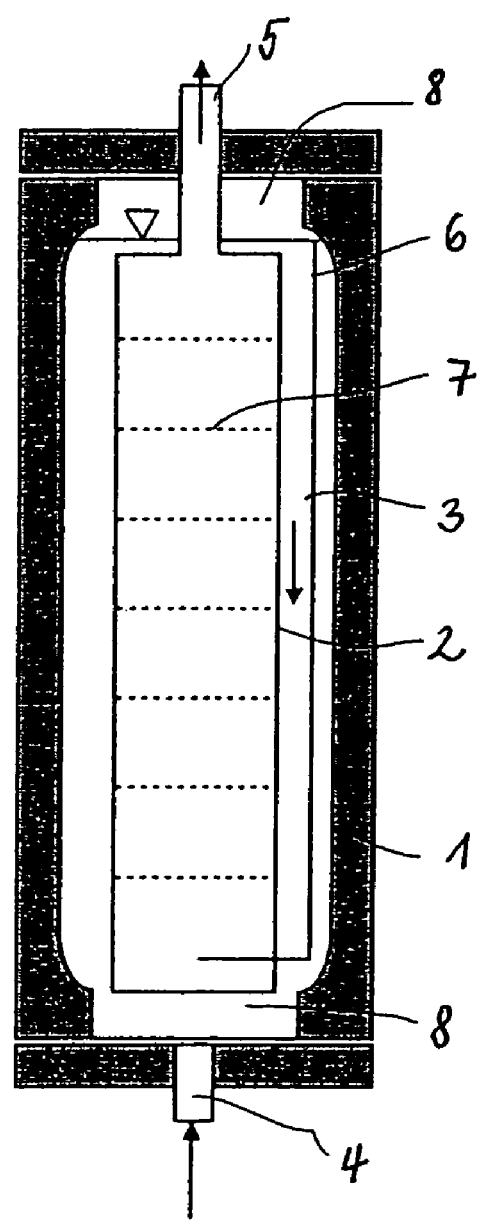

This is a divisional application of application Ser. No. 10/073,248, filed Feb. 13, 2002, now U.S. Pat. No. 7,015,361, the entire disclosure of which is hereby incorporated by reference.

The present invention relates to a process for the hydroformylation of olefins having at least 6 carbon atoms and to an apparatus for carrying out the process.

Hydroformylation or the oxo process is an important industrial process and is employed for preparing aldehydes from olefins, carbon monoxide and hydrogen. These aldehydes can, if desired, be hydrogenated by means of hydrogen to produce the corresponding alcohols in the same process step or subsequently in a separate hydrogenation step. Hydroformylation is carried out in the presence of catalysts which are homogeneously dissolved in the reaction medium. Catalysts used are generally the carbonyl complexes of metals of transition group VIII, in particular Co, Rh, Ir, Pd, Pt or Ru, which may be unmodified or modified with, for example, amine- or phosphine-containing ligands. A summary of processes employed in industry may be found in J. Falbe, "New Syntheses with Carbon Monoxide", Springer Verlag 1980, p. 162 ff.

While short-chain olefins can be hydroformylated relatively easily, the hydroformylation of higher olefins sometimes presents problems. This is due to the decrease in the reaction rate as the chain length increases and the proportion of internal, nonterminal double bonds rises and also to the increase in the viscosity of the starting materials and the reaction mixture. To achieve satisfactory conversions, it is therefore necessary to employ long residence times, but these adversely affect the selectivity as a result of undesirable secondary reactions, in particular the formation of high-boiling reaction by-products. Furthermore, the purity demands made of the direct process product are very high because, due to its high viscosity, it is virtually impossible to fractionate and thus has to be used essentially without further purification. A reduction in the reaction volume is of particular importance for the economics of the process, since large reaction volumes are very expensive at the high pressures needed in the process.

To keep the reaction volume as small as possible and to increase the space-time yield, it has therefore been proposed that a reactor cascade be used in place of a continuous stirred tank reactor (CSTR). Cascading can be achieved by various methods, but these have the disadvantages described below:

A customary method is cascading by connecting reactors in series. However, this method is the most expensive since the capital cost of the individual reactors, the associated connections and the instrumentation required increase with the number of reactors.

WO 97/20793 describes a process for carrying out hydroformylations in a single reactor in which cascading is provided by horizontally arranged perforated plates. The configuration of the stirring elements of the centrally arranged stirrer are matched to the openings and intermediate spaces of the perforated plates. Such a reactor has, in particular, the following disadvantages: high-pressure apparatuses are generally constructed as cylinders whose ends have a lower diameter than the central part, i.e. as double-necked apparatuses. It is very difficult in engineering terms to install horizontal perforated plates whose diameter corresponds to that of the middle section through such necks. Cascading by means of horizontal perforated plates has the further disadvantage that these perforated plates maintain a high pressure in the event of an emergency depressurization and therefore have to be designed with very great thicknesses. Further, the impeller shaft extending into the reaction chamber has to be inserted pressure-tight.

It is an object of the present invention to provide a process for the hydroformylation of olefins having at least 6 carbonatoms which gives a very high conversion at a given reactor volume. A further object is to provide an apparatus for carrying out the process which has low capital and operating costs.

We have found that this object is achieved by a continuous process for the hydroformylation of olefins having at least 6carbon atoms in the presence of a homogeneous catalyst, wherein a) a vertical tall cylindrical reactor (1) whose interior space is divided by means of internals (2) into at least two reaction chambers which extend essentially in the longitudinal direction of the reactor is used, b) at least one olefin is introduced into the reactor together with synthesis gas at the lower end of the first reaction chamber, c) a partially reacted reaction mixture is conveyed from the upper end of a reaction chamber to the lower end of a next reaction chamber; and d) the hydroformylated olefin is taken off at the upper end of the last reaction chamber. Olefins having at least 6, e.g. from 9 to 20, carbon atoms can be hydroformylated by the process of the present invention. For practical reasons, the maximum chain length is generally limited to about 700 carbon atoms. The process of the present invention is particularly useful for the hydroformylation of isomeric olefin mixtures prepared by oligomerization of lower olefins such as propene and butenes. Typical oligomers which are suitable as starting materials for the present process include, inter alia, propene dimer, propene trimer and propene tetramer, butene dimer, butene trimer and butene tetramer and also cooligomers of propenes and butenes. The oligomers of butenes can be obtained industrially by known oligomerization processes, e.g. by the Octol® process of Hüls and the Dimersol® process of IFP. Furthermore, linear long-chain olefins having a terminal double bond which are obtainable, for example, by the SHOP® process or Ziegler processes or linear long-chain olefins having an internal double bond can also be hydroformylated by the process of the present invention.

Further preferred starting olefins are essentially monounsaturated polyalkylenes having from 30 to 700 carbon atoms, in particular polybutene or polyisobutene.

The process of the present invention is homogeneously catalyzed. In general, this is achieved by introducing a suitable catalyst or catalyst precursor into the reactor together with the olefin and the synthesis gas. There are no significant restrictions in respect of the catalysts or catalyst precursors which can be used. In particular, cobalt catalysts, preferably cobalt carbonyls or hydridocobalt carbonyl or their precursors, in particular cobalt(II) salts such as cobalt (II) formate, cobalt(II) acetate or cobalt(II) ethylhexanoate, are used in a manner known per se.

The catalyst is advantageously introduced as a solution in the starting olefin or an organic solvent which may be used in addition. For this purpose, it is possible to bring an aqueous cobalt(II) salt solution into contact with synthesis gas outside the reactor to form a hydroformylation-active cobalt catalyst and simultaneously or subsequently bring the aqueous solution containing the cobalt catalyst into contact with the starting olefin and/or the organic solvent so that the cobalt catalyst is extracted into the organic phase.

The prior formation of the catalyst is preferably carried out at from 50 to 200° C., in particular from 100 to 160° C., under pressures of from 100 to 400 bar, in particular from 200 to 300 bar.

Suitable apparatuses are customary apparatuses for gas/liquid reactions, e.g. stirred vessels provided with a sparging stirrer, bubble columns or trickle-bed columns. The precarbonylation is advantageously carried out in the presence of activated carbon, zeolites or basic ion exchangers loaded with cobalt carbonyl, as described in DE-A 2139630. The cobalt catalyst is then extracted from the resulting aqueous solution containing cobalt(II) salts and cobalt catalyst into the olefins to be hydroformylated and/or the organic solvent which may be used in addition.

In many cases it is preferable, in view of the reduced process engineering costs, to carry out the formation of the cobalt catalyst, the extraction of the cobalt catalyst in the organic phase and the hydroformylation of the olefins in one step by introducing the aqueous cobalt(II) salt solution, the olefins, synthesis gas and any organic solvent used together into the reactor. The starting materials are introduced into the reaction zone so that good phase mixing occurs and a very high mass transfer area is generated. For introducing the starting material into the reactor, it is possible to use the introduction devices known to those skilled in the art, e.g. turbulence tubes filled with packing elements or mixing nozzles for multiphase systems.

To remove the cobalt catalyst after the reaction, the crude reaction product is appropriately depressurized to intermediate pressure, in general from 10 to 30 bar, after leaving the reaction zone and is passed to a cobalt removal stage. In the cobalt removal stage, the reaction product is freed of cobalt carbonyl complexes by means of air or oxygen, preferably at from 90 to 130° C., in the presence of an aqueous, weakly acidic cobalt(II) salt solution. The removal of cobalt can, if desired, be carried out in a pressure vessel filled with packing elements, e.g. Raschig rings, in which a very high mass transfer area is generated. The organic product phase is separated from the aqueous phase in a downstream phase separation vessel. In the cobalt removal stage, the hydroformylation-active cobalt catalyst is decomposed to form cobalt(II) salts, predominantly cobalt(II) formate. The aqueous cobalt(II) salt solution is advantageously returned to the reaction zone or the catalyst formation stage.

As an alternative, it is possible to use rhodium catalysts which may be modified by nitrogen- or phosphorus-containing ligands. The rhodium catalyst is generally separated from the hydroformylation product by distillation, in which the rhodium catalyst remains as residue together with high-boiling constituents.

Synthesis gas is an industrially available mixture of carbon monoxide and hydrogen. The composition of the synthesis gas used in the process of the present invention can vary within a wide range. The molar ratio of carbon monoxide to hydrogen is generally from about 10:1 to 1:10, in particular from 2.5:1 to 1:2.5. A preferred ratio is about 1:1.5.

As organic solvent which may be used in addition, it is possible to use inert hydrocarbons such as paraffin fractions, aromatic hydrocarbons such as benzene, toluene or xylene, or an aldehyde and/or alcohol, in particular the hydroformylation product of the olefin used. High-boiling by-products of the hydroformylation can also be used as solvent. The use of a solvent may be advantageous, for example, for reducing the viscosity in the case of long-chain olefins.

The temperature in the hydroformylation is generally from 100 to 250° C., in particular from 145 to 200° C. The reaction is preferably carried out at a pressure in the range from 20 to 400 bar, in particular from 200 to 300 bar.

The preheated or unpreheated starting olefin, synthesis gas and, if appropriate, catalyst or catalyst precursor are fed into a vertical, tall cylindrical reactor which has at least two reaction chambers. According to the present invention, the reaction chambers extend essentially in the longitudinal direction of the reaction and are formed by division of the interior space of the reactor by means of internals which are arranged essentially in the longitudinal direction of the reactor. "Essentially in the longitudinal direction of the reactor" means that the reaction chambers have their longest dimension in the direction of the longitudinal axis of the reactor and the length of a reaction chamber is more than 50%, preferably more than 60%, of the length of the reactor. The internals in each case form a reaction chamber enclosed on all sides with an inlet for the reaction mixture at one end and an outlet for the reaction mixture at the opposite end. The reaction mixture is thus firstly fed in at the bottom of a first reaction chamber, flows through this from the bottom upward and at the upper end of this chamber is fed via suitable means for the recirculation of fluid to a second reaction chamber at its lower end. From this second reaction chamber, the reaction mixture can be discharged from the reactor, but it is also possible to configure the reactor and the process so that the reaction mixture is conveyed from the upper end of the second reaction chamber via means for the recirculation of fluid to the lower end of a third reaction chamber, if desired flows in an analogous manner through further reaction chambers and is finally discharged from the upper part of the last reaction chamber.

The internals are preferably configured as cylinders which are closed at both ends and have inlet and outlet openings at opposite ends. There are in principle no restrictions in respect of the arrangement of the internals in the reactor cross section; the internals can be arranged next to one another, preferably distributed uniformly over the reactor cross section, but are particularly preferably arranged concentrically to one another and to the outer wall of the reactor.

In a preferred embodiment, the internals form an internal cylinder which is closed at both ends and has an inlet at the lower end and an outlet at the upper end. The reaction mixture is particularly preferably first fed into the intermediate space between the interior wall of the reactor and internals, conveyed from the upper end of the intermediate space via means for the recirculation of fluid to a second reaction chamber at its lower end, if desired conveyed from the upper end of this to further reaction chambers through which it is passed from the bottom upward and finally discharged from the reactor.

In this embodiment, the second reaction chamber thus serves as an after-reaction zone, i.e. a zone for the completion of the olefin conversion achieved in the first reaction chamber, without undesirable backmixing with the contents of the first reaction chamber.

In one possible variant, unreacted synthesis gas can be taken, e.g. drawn off under suction, from the gas space at the upper end of one or more reaction chambers with the exception of the last reaction chamber, compressed and fed back into the reactor from below. This measure can be employed regardless of the number of reaction chambers present. If only two reaction chambers are present, unreacted synthesis gas is, for example, taken off from the upper region of the intermediate space between the interior wall of the reactor and internals and fed back into the same reaction chamber in its lower region. In the case of more than two reaction chambers, unreacted gas can be taken off from one or more of the reaction chambers, in each case in its upper part, but not from the reaction chamber which is the last through which the reaction mixture flows. The recirculation of synthesis gas increases the turbulence in the first reaction chamber and ensures intimate contact of the gaseous and liquid phases.

The compression of the recirculated, unreacted synthesis gas can advantageously be carried out by means of a jet pump, in which case it is particularly useful to operate the jet pump by means of the feed stream comprising olefin and freshly introduced synthesis gas. The jet pump can be located in the lower region of the reactor, but it is also possible to install it underneath (and outside) the reactor.

In a further embodiment, it is possible for the jet pump to be operated using not only the feed stream but also partially reacted reaction mixture which is, for example, drawn off from the reaction at the lower end of the first reaction chamber by means of a circulation pump. The reaction mixture which has been drawn off is particularly preferably firstly passed through a heat exchanger to remove heat before being fed to the jet pump.

Between the individual reaction chambers in the interior of the reactor, the reactor is provided with means for the recirculation of fluid which in each case convey the reaction mixture from the upper end of a reaction chamber to the lower end of a next reaction chamber. These means for the recirculation of fluid are particularly preferably configured as downpipes or siphons. The downpipes are configured so that their upper edge keeps the liquid level, i.e. the position of the liquid/gas phase boundary, in the respective reaction chamber constant. Should the liquid level drop below the upper edge of the downpipe, the gas pressure which builds up causes more unreacted synthesis gas to be passed through the downpipe into the next reaction chamber until the liquid level once again reaches the upper end of the downpipe, and vice versa. In this way, control of the level is achieved without complicated engineering measures.

The tall cylindrical reactor preferably has an aspect ratio, i.e. a ratio of length to diameter, l/d, of from about 3:1 to 30:1, in particular from about 5:1 to 10:1.

The internals in the reactor are preferably dimensioned so that the ratio of the volume of the first reaction chamber to that of the second reaction chamber or of the volumes of two further successive reaction chambers is from 4:1 to 1:4, preferably from 1.5:1 to 1:1.5, particularly preferably about 1:1.

The dimensions of the internals in the longitudinal direction are designed so that the height of the second reaction chamber (of the further reaction chambers) is more than 50%, in particular more than 60%, of the height of the reactor, particularly preferably from 80 to 95% of the height of the reactor.

In a preferred embodiment, additional cascading of the last reaction chamber, e.g. the second reaction chamber, can be achieved by means of horizontal diffusion-inhibiting devices, e.g. perforated plates which are preferably arranged so as to be equidistant from one another. The number of perforated plates can be from 1 to 10, particularly preferably from 3 to 5. This measure has a conversion-promoting effect on the hydroformylation reaction, so that a further increase in conversion can be achieved for a given reaction volume. The horizontal perforated plates can advantageously be mounted in the internals forming the further reaction chambers before these internals are installed in the reactor, so that assembly costs are significantly reduced. They can be mounted in a removable fashion by means of appropriate flange connections or else can be welded directly onto the internals.

The interior of the reactor of the present invention can be provided with means for the indirect cooling of the reaction chambers. Such means are particularly preferably provided in the first reaction chamber through which the reaction mixture flows. They are preferably in the form of cooling coils through which a cooling medium flows. The cooling coils can be fixed to the internals, e.g. welded onto them, or be installed at a distance from the internals.

Figure 2:
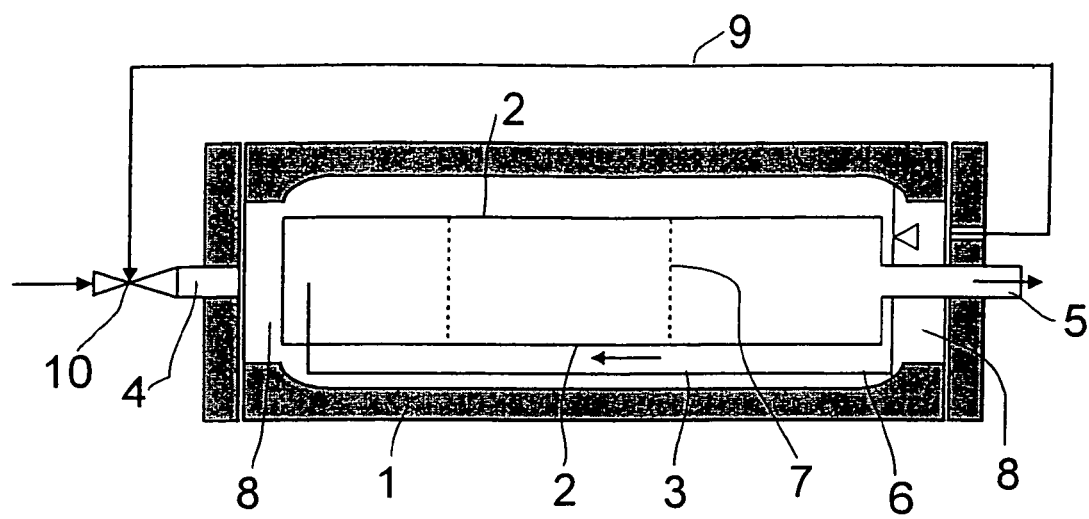
Figure 3:
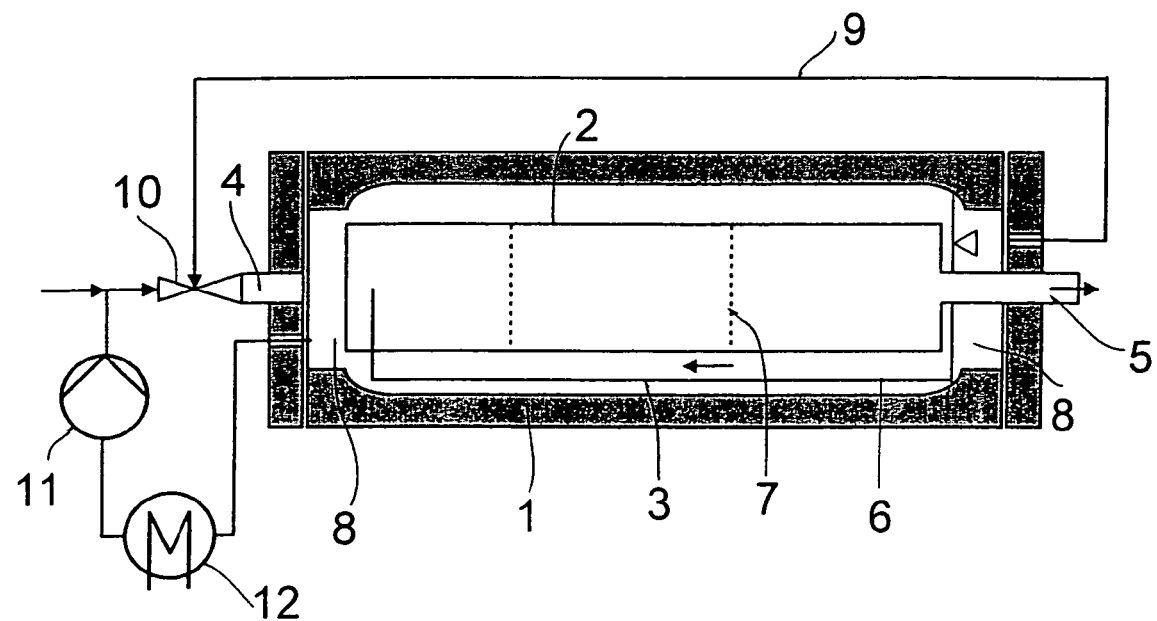
Figure 4:
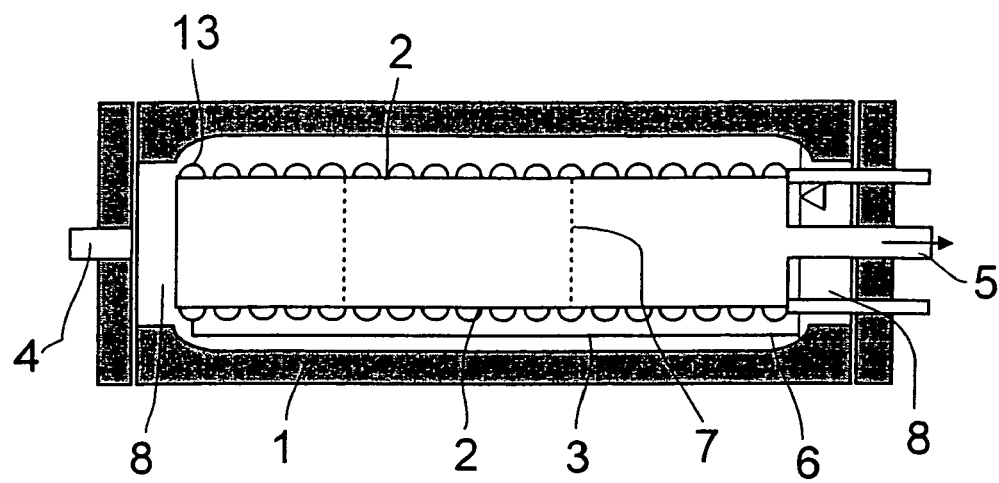
Figure 5:
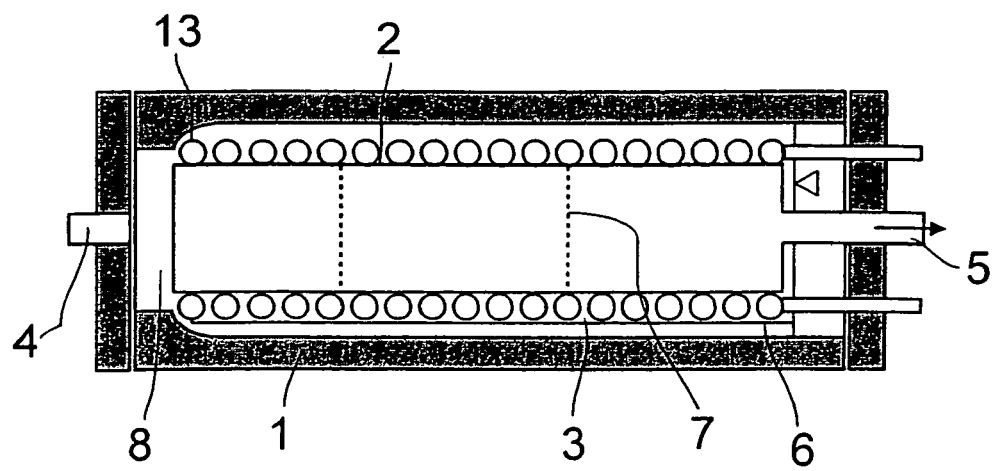
Figure 6:
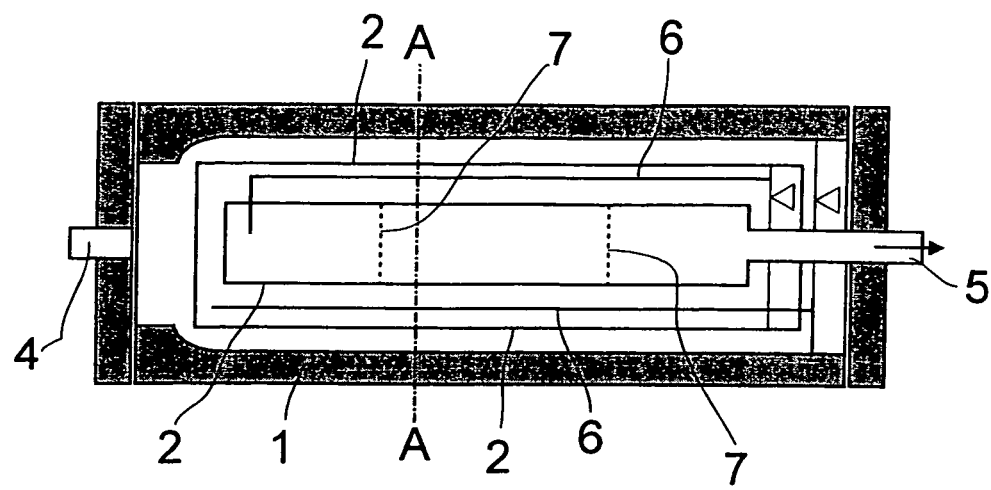
Figure 6A:
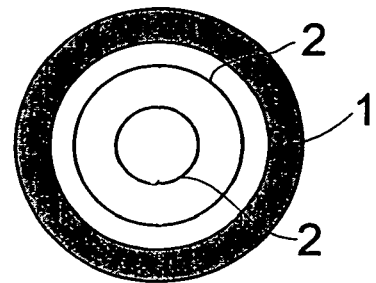
Figure 7A:
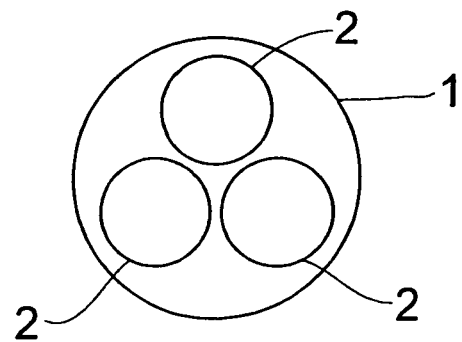

The invention is illustrated below with the aid of a drawing and examples:

In the drawing:

FIG. 1 schematically shows a longitudinal section of a preferred embodiment of an apparatus according to the present invention, FIG. 2 shows a longitudinal section of a further preferred embodiment of an apparatus according to the present invention with recirculation of gas by means of a jet pump, FIG. 3 shows a further embodiment of the apparatus from FIG. 2 with additional recirculation of part of the reaction mixture via the jet pump, FIG. 4 shows a longitudinal section of a further preferred embodiment with cooling coils fixed to the internals, FIG. 5 shows a variant with cooling coils which are not fixed to the internals, FIG. 6 shows both a longitudinal section and a cross section (FIG. 6a) of a variant with three reaction chambers and FIG. 7a shows a cross section through a reactor according to the present invention having no concentric internals.

In the figures, identical reference numerals are used to denote the same features.

FIG. 1 shows, by way of example, a longitudinal section of a reactor 1 according to the present invention having a neck 8 at each end of the reactor, internals 2 which form a concentric internal cylinder closed at both ends and an inlet 4 into the intermediate space 3 between the interior wall of the reactor and the internals 2 and an outlet 5 from the reaction chamber bounded by the internals 2, and having means 6 for the recirculation of fluid from the upper part of the intermediate space between the interior wall of the reactor and internals 2 to the lower end of the reaction chamber bounded by the internals 2 and also horizontal perforated plates 7, with seven perforated plates being depicted by way of example.

FIG. 2 shows a longitudinal section of a further preferred embodiment which additionally has a return line for gas 9 from the upper region of the intermediate space between the interior space of the reactor and internals 2, with the return line 9 leading to a jet pump 10 which is installed underneath the reactor and is operated by means of the liquid feed mixture.

FIG. 3 shows a longitudinal section of a further preferred embodiment in which the jet pump 10 located underneath the reactor is additionally driven by liquid reaction mixture which is taken off from the lower part of the reactor by means of a circulation pump 11 and fed to the jet pump, and the liquid reaction mixture is firstly cooled by means of a heat exchanger 12.

The embodiment shown in longitudinal section in FIG. 4 additionally has cooling coils 13 which are fixed to the internals 2 and thus cool both the intermediate space between the interior wall of the reactor and internals 2 and the interior space of the reactor bounded by the internals 2.

In contrast, the variant shown in FIG. 5 has cooling coils 13 which are located only in the intermediate space between the interior wall of the reactor and internals 2 and thus cool predominantly this intermediate space.

FIG. 6 shows an illustrated embodiment having three reaction chambers which are formed by concentric arrangement of two cylindrical internals 2 within the reactor 1. The cross section A/A through the reactor of FIG. 6 (FIG. 6a) clearly shows the concentric arrangement of the internals 2.

On the other hand, FIG. 7a shows a cross section through a reactor having three internals 2 which are not installed concentrically in the reactor 1.

The present invention thus provides a process which gives an improved space-time yield and achieves an increase in conversion and selectivity. The apparatus of the present invention has lower capital and operating costs than do known apparatuses.

A particularly advantageous aspect is the improvement in the mass transfer between liquid reaction medium and gas phase as a result of the division according to the present invention of the reactor cross section into a plurality of zones by means of the internals arranged essentially in the longitudinal direction of the reactor. This achieves an increase in the cross-sectional throughput in the zones, resulting in improved mass transfer. In this way, the very low gas content and mass transfer areas in known apparatuses can be increased by a factor of two or more without the use of rotating parts, for example stirrers. The disadvantages associated with the use of rotating parts, particularly in the case of high-pressure apparatuses, can thus be avoided.

EXAMPLE

The invention is illustrated by the following mathematical simulation. The simulation is based on a kinetic model of the hydroformylation of polyisobutene, which has been set up by mathematical fitting of a large number of experimental measurements. The simulation was carried out for a mixture of 80% by weight of a reactive, only slightly branched polyisobutene $A_1$ and 20% by weight of a less reactive, more strongly branched polyisobutene $A_2$ as feed. A 10% excess of synthesis gas (molar ratio of $CO/H_2=1:1$), a reaction temperature of 130° C. and a pressure of 280 bar were employed as basis for the simulation. It was assumed that the reaction rates of the reaction of $A_1$ and $A_2$ to form the respective hydroformylation product are proportional to the mole fractions of $A_1$ and $A_2$, respectively. Any dependence on the CO or $H_2$ concentration was disregarded. The simulation was carried out on the basis of the reaction volume remaining unchanged in the reaction. The mass flow of olefin feed and catalyst solution (aqueous cobalt(II) formate solution) was in each case set to 6000 kg/h.

In case I, the simulation was carried out for a reactor without internals and having a volume of 30 m³ and total backmixing. In case II, the reactor was divided into four ideally mixed substages having volumes of 15 m³, 5 m³, 5 m³ and 5 m³. The inlet concentrations of the olefin feed and the amounts of catalyst are the same in both reactor configurations.

The results obtained are summarized in the following table.

| Example | Conversion of $A_1$ | Conversion of $A_2$ | Total conversion of $A_1 + A_2$ |
|---------|---------------------|---------------------|--------------------------------|
| I       | 78.3%               | 26.5%               | 67.9%                          |
| II      | 91.3%               | 28.9%               | 78.8%                          |

It can be seen that both the individual conversions and the total conversion are higher in the case of the cascading according to the present invention of the reactor at the same reaction volume.

We claim:

1. A vertical cylindrical reactor having a ratio of length to diameter of from about 3:1 to 30:1 for the hydroformylation of olefins having at least 6 carbon atoms wherein said hydroformylation is performed in the presence of a homogenous catalyst, comprising:
   a) internals by which the interior space of the reactor is divided into at least two reaction chambers which extend essentially in the longitudinal direction of the reactor, the internals being configured as at least one cylinder which is closed at both ends, the at least two reaction chambers comprising a first reaction chamber and a last reaction chamber,
   b) an inlet in a lower end of the first reaction chamber for introduction of at least one olefin together with synthesis gas, the inlet comprising at least one mixing nozzle for mixing at least one olefin with synthesis gas,
   c) a recirculator for the recirculation of fluid from an upper end of the first reaction chamber to lower end of a next of the reactions chambers, without back-mixing with a content of the first reaction chamber, the recirculation being configured as at least one down-pipe so that the upper edge of the down pipe keeps the liquid/gas phase boundary in the first reaction chamber constant such that if the liquid level drops below the upper edge of the down-pipe, more unreacted synthesis gas is passed through the down-pipe into the next reaction chamber until the liquid level again reaches the upper edge of the down-pipe, and vice versa, and
   d) an outlet for taking off hydroformylated olefin at an upper end of the last reaction chamber.

2. The reactor as claimed in claim 1, wherein the at least one cylinder dividing the interior space of the reactor is arranged essentially concentrically to the outer wall of the reactor.

3. The reactor as claimed in claim 1, having a ratio of length to diameter of about 5:1 to 10:1.

4. The reactor as claimed in claim 1, wherein the last reaction chamber is cascaded by means of horizontal perforated plates located at a distance from one another.

5. The reactor as claimed in claim 1, wherein the height of a second and any further reaction chambers, of said at least two reaction chambers, is more than 50% of the height of the reactor.

* * * * *

UNITED STATES PATENT AND TRADEMARK OFFICE
CERTIFICATE OF CORRECTION

PATENT NO. : 7,351,384 B2  
APPLICATION NO. : 11/218532  
DATED : April 1, 2008  
INVENTOR(S) : Zehner et al.

It is certified that error appears in the above-identified patent and that said Letters Patent is hereby corrected as shown below:

On the Title Page item 57, in the Abstract:
 in line 1: "bydroformylated" should read --hydroformylated--
 in line 4: "internals (2)." should read --internals (2)--

Signed and Sealed this

First Day of July, 2008

JON W. DUDAS  
*Director of the United States Patent and Trademark Office*